(12) United States Patent
Morello et al.

(10) Patent No.: US 8,190,390 B2
(45) Date of Patent: *May 29, 2012

(54) DEVICE, METHOD, AND SYSTEM FOR CALIBRATION OF A FLOW METER USED IN CONJUNCTION WITH A VENTRICULAR ASSIST DEVICE

(75) Inventors: Gino Morello, Leonia, NJ (US); Bryan Lynch, Houston, TX (US); Robert Benkowski, Houston, TX (US)

(73) Assignee: Micromed Technology, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/944,348

(22) Filed: Nov. 11, 2010

(65) Prior Publication Data

US 2011/0093230 A1   Apr. 21, 2011

Related U.S. Application Data

(62) Division of application No. 12/354,259, filed on Jan. 15, 2009, now Pat. No. 7,856,335.

(60) Provisional application No. 61/023,491, filed on Jan. 25, 2008.

(51) Int. Cl.
*G01F 25/00* (2006.01)

(52) U.S. Cl. .................. 702/100; 73/1.34; 73/861.357; 700/286; 702/45; 703/11

(58) Field of Classification Search .............. 702/45, 702/85, 100; 703/11; 73/1.34, 861.357; 128/204.18; 210/646; 600/16, 17, 431, 504, 600/505; 604/6.07; 700/286

See application file for complete search history.

(56) References Cited

U.S. PATENT DOCUMENTS

| 4,142,412 A | 3/1979 | McLeod et al. |
| 4,237,729 A | 12/1980 | McLeod et al. |
| 4,778,449 A | 10/1988 | Weber et al. |
| 4,865,581 A | 9/1989 | Lundquist et al. |

(Continued)

FOREIGN PATENT DOCUMENTS

DE     10149292     5/2003

(Continued)

OTHER PUBLICATIONS

Bichlmayer, K., International Search Report for International Patent Application No. PCT/US2009/000473, dated Jul. 10, 2009, European Patent Office.

(Continued)

*Primary Examiner* — John H Le
(74) *Attorney, Agent, or Firm* — Sutton McAughary Deaver PLLC

(57) ABSTRACT

A blood flow calibration system 500 including a computer 400 operable to determine and store calibration data for a flow meter 124, a test system 530 operable to simulate blood flow for the flow meter 124, thereby allowing the computer 400 to determine the calibration data, and a programmer 300 operable to transfer the calibration data from the computer 400 to the flow meter 124. The flow meter 124 preferably includes a power management circuit 348$a,b$ operable to detect whether the flow meter 124 is powered. In the event that the flow meter 124 is unpowered, the power management circuit 348$a,b$ is preferably able to supply power to a portion of the flow meter 124 in order to transfer the calibration data thereto.

21 Claims, 12 Drawing Sheets

U.S. PATENT DOCUMENTS

| | | | |
|---|---|---|---|
| 4,965,756 A | 10/1990 | Pearman et al. | |
| 5,007,927 A | 4/1991 | Badylak et al. | |
| 5,011,468 A | 4/1991 | Lundquist et al. | |
| 5,012,667 A * | 5/1991 | Kruse | 73/1.34 |
| 5,059,167 A | 10/1991 | Lundquist et al. | |
| 5,150,292 A | 9/1992 | Hoffmann et al. | |
| 5,284,423 A | 2/1994 | Holdsworth et al. | |
| 5,509,424 A | 4/1996 | Al-Ali | |
| 5,527,159 A | 6/1996 | Bozeman, Jr. et al. | |
| 5,625,569 A * | 4/1997 | Trimmer et al. | 700/286 |
| 5,682,899 A | 11/1997 | Nashef et al. | |
| 5,692,882 A | 12/1997 | Bozeman, Jr. et al. | |
| 5,947,892 A | 9/1999 | Benkowski et al. | |
| 5,960,403 A | 9/1999 | Brown | |
| 6,183,412 B1 | 2/2001 | Benkowski et al. | |
| 6,279,574 B1 | 8/2001 | Richardson et al. | |
| 6,605,032 B2 | 8/2003 | Benkowski et al. | |
| 6,623,420 B2 | 9/2003 | Reich et al. | |
| 6,652,447 B2 | 11/2003 | Benkowski et al. | |
| 7,204,798 B2 | 4/2007 | Zdeblick et al. | |
| 7,856,335 B2 * | 12/2010 | Morello et al. | 702/100 |
| 2004/0084372 A1 | 5/2004 | Connell et al. | |
| 2006/0142985 A1* | 6/2006 | O'Donnell et al. | 703/11 |
| 2007/0017304 A1* | 1/2007 | Kumpfmuller | 73/861.357 |
| 2007/0197854 A1 | 8/2007 | Marseille et al. | |
| 2007/0282298 A1 | 12/2007 | Mason | |
| 2008/0221822 A1 | 9/2008 | Laverdiere et al. | |

FOREIGN PATENT DOCUMENTS

| | | |
|---|---|---|
| GB | 2116720 | 9/1983 |

OTHER PUBLICATIONS

Bichlmayer, K., Written Opinion for International Patent Application No. PCT/US2009/000473, dated Jul. 10, 2009, European Patent Office.

* cited by examiner

DEVICE, METHOD, AND SYSTEM FOR CALIBRATION OF A FLOW METER USED IN CONJUNCTION WITH A VENTRICULAR ASSIST DEVICE

CROSS REFERENCE TO RELATED APPLICATIONS

This application is a divisional of and claims the benefit of and priority to U.S. Provisional patent application Ser. No. 12/354,259, filed on Jan. 15, 2009, which claims the benefit of and priority to U.S. Provisional Patent Application No. 61/023,491, filed on Jan. 25, 2008. The entire disclosures of these applications are incorporated herein by specific reference.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

1. Field of the Invention

The inventions disclosed and taught herein relate generally to Ventricular Assist Devices (VAD) and more specifically relate to the programming of VAD controllers.

2. Description of the Related Art

Artificial heart and other implantable blood pump systems are generally employed either to completely replace a human heart that is not functioning properly, or to boost blood circulation in patients whose heart still functions but is not pumping blood at an adequate rate. The rate at which such systems pump blood can be critical. As such, controllers for these systems need to be able to accurately monitor and control the rate at which these systems pump blood.

For example, U.S. Patent Application No. 20070282298 teaches a "method of and apparatus for controlling the speed of a rotary blood pump, which comprises the measuring the speed and/or power of said pump, calculating an array of system parameters derived from the measured speed, analyzing these parameters, and if the analysis indicates ventricular collapse or imminent ventricular collapse, then the speed of said pump is altered, to minimize the risk of the collapse occurring." Abstract.

U.S. Patent Application No. 20070197854 teaches a "supplemental blood flow system for assisting with blood circulation in a patient. The system includes a supplemental blood flow device implantable in the patient and a controller for directing electrical power to the supplemental blood flow device and controlling the flow rate of blood through the device. The controller includes first and second power inlets and a power outlet. The power outlet is adapted to be coupled to an electrical line leading to the supplemental blood flow device. A portable programming module may be coupled to at least one of the first and second power inlets and operable to allow pump operating parameters stored in the controller to be changed according to the needs of the patient." Abstract.

The present disclosure addresses shortcomings associated with the prior art.

BRIEF SUMMARY OF THE INVENTION

One aspect of the inventions disclosed herein comprises a blood flow calibration system including a computer operable to determine and store calibration data for a flow meter, a test system operable to simulate blood flow for the flow meter, thereby allowing the computer to determine the calibration data, and a programmer operable to transfer the calibration data from the computer to the flow meter. The flow meter preferably includes a power management circuit operable to detect whether the flow meter is powered. In the event that the flow meter is unpowered, the power management circuit is preferably able to supply power to a portion of the flow meter in order to transfer the calibration data thereto.

DETAILED DESCRIPTION

Figure 1:
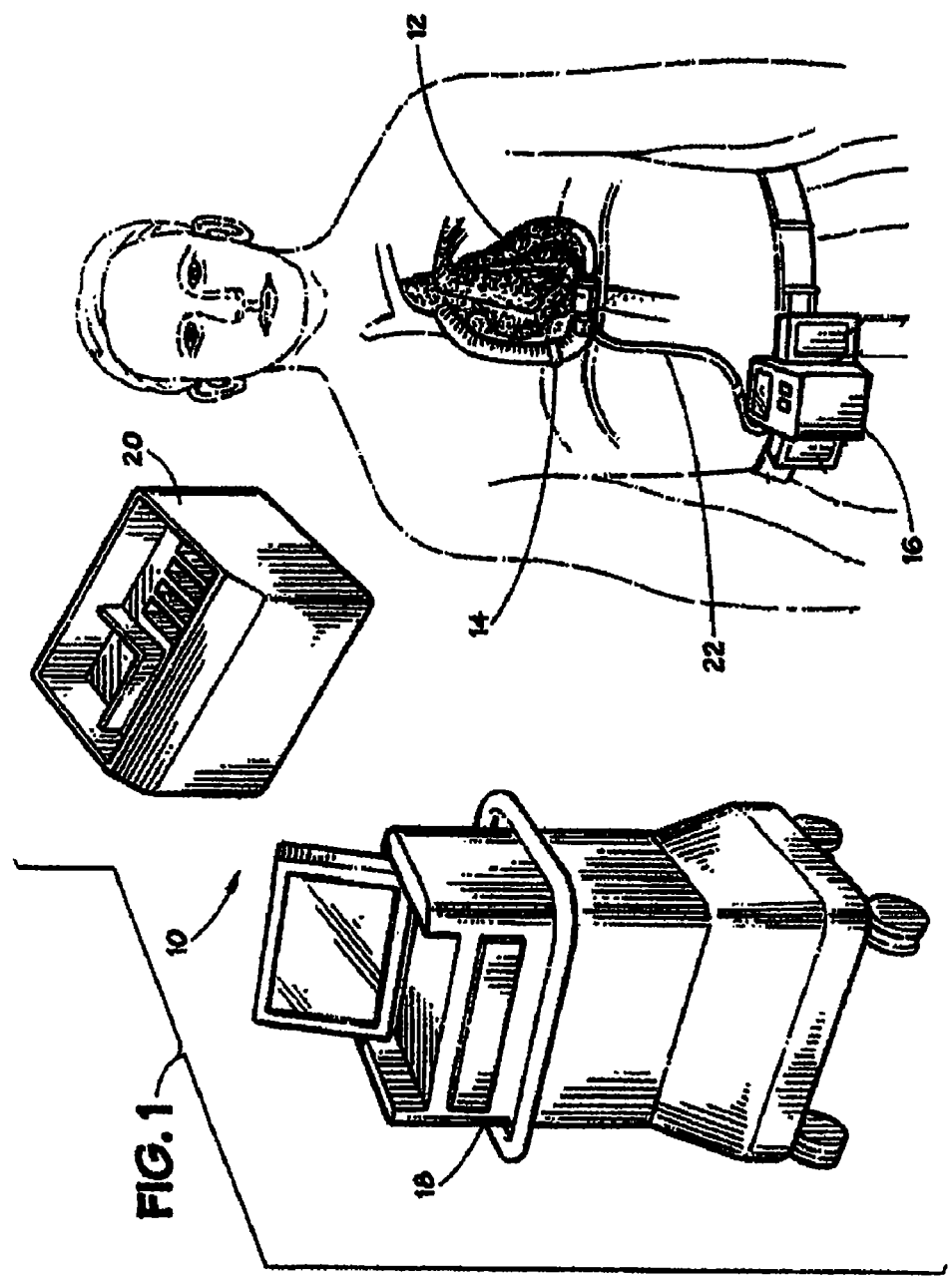
FIG. 1 illustrates portions of a heart pump system in accordance with certain teachings of the present disclosure.

The Figures described above and the written description of specific structures and functions below are not presented to limit the scope of what Applicants have invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation and location from time to time. While a developer's efforts might be complex and time-consuming in an absolute sense, such efforts would be, nevertheless, a routine undertaking for those of skill in this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims.

Particular embodiments of the invention may be described below with reference to block diagrams and/or operational illustrations of methods. It will be understood that each block of the block diagrams and/or operational illustrations, and combinations of blocks in the block diagrams and/or operational illustrations, can be implemented by analog and/or digital hardware, and/or computer program instructions. Such computer program instructions may be provided to a processor of a general-purpose computer, special purpose computer, ASIC, and/or other programmable data processing system. The executed instructions may create structures and functions for implementing the actions specified in the block diagrams and/or operational illustrations. In some alternate implementations, the functions/actions/structures noted in the figures may occur out of the order noted in the block diagrams and/or operational illustrations. For example, two operations shown as occurring in succession, in fact, may be executed substantially concurrently or the operations may be executed in the reverse order, depending upon the functionality/acts/structure involved.

Computer programs for use with or by the embodiments disclosed herein may be written in an object oriented programming language, conventional procedural programming language, or lower-level code, such as assembly language and/or microcode. The program may be executed entirely on a single processor and/or across multiple processors, as a stand-alone software package or as part of another software package.

A blood flow calibration system is disclosed comprising a computer operable to determine and store calibration data for a flow meter, a test system operable to simulate blood flow for the flow meter, thereby allowing the computer to determine the calibration data, and a programmer operable to transfer the calibration data from the computer to the flow meter. The programmer preferably includes a power management circuit operable to detect whether the flow meter is powered. In the event that the flow meter is unpowered, the power management circuit is preferably able to supply power to a portion of the flow meter in order to transfer the calibration data thereto.

FIG. 1 is an illustration of an exemplary heart pump system 10, which as shown, functions as a ventricle assist device (VAD). The system 10 includes components designed to be implanted within a human body and components external to the body. The components of the system 10 that are implantable include a rotary pump 12 (or "VAD pump") and a flow sensor 14. The external components include a portable pump controller module 16. The implanted components are connected to the pump controller 16 via a percutaneous cable 22.

Suitable pumps include various embodiments of pumps disclosed in U.S. Pat. Nos. 5,527,159; 5,947,892 or 5,692,882; the subject matter of each of which is incorporated herein by reference. Exemplary implantable pump systems and control methods are disclosed in U.S. Pat. Nos. 6,652,447; 6,605,032 and 6,183,412; each also incorporated herein by reference. Implantable centrifugal pumps or pulsatile pumps may also be employed in conjunction with the present disclosure. Such pump systems and control methods may form part of an Artificial Heart System, such as that disclosed in U.S. patent application Ser. No. 11/916,958, filed Jun. 8, 2005, also incorporated by reference.

Figure 2:
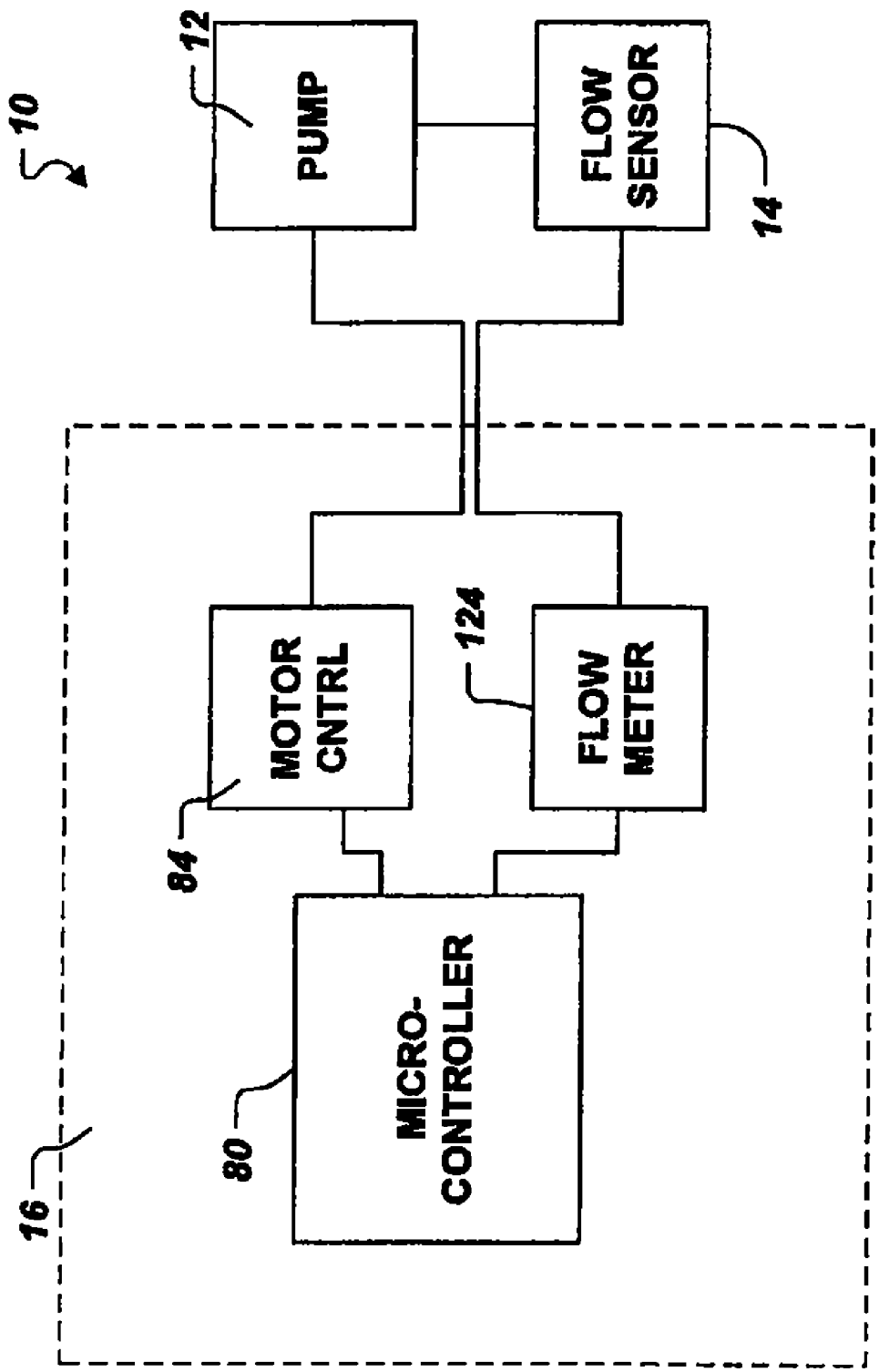
FIG. 2 is a block diagram of portions of a pump and pump controller in accordance with the teachings of the present disclosure.
Figure 3:
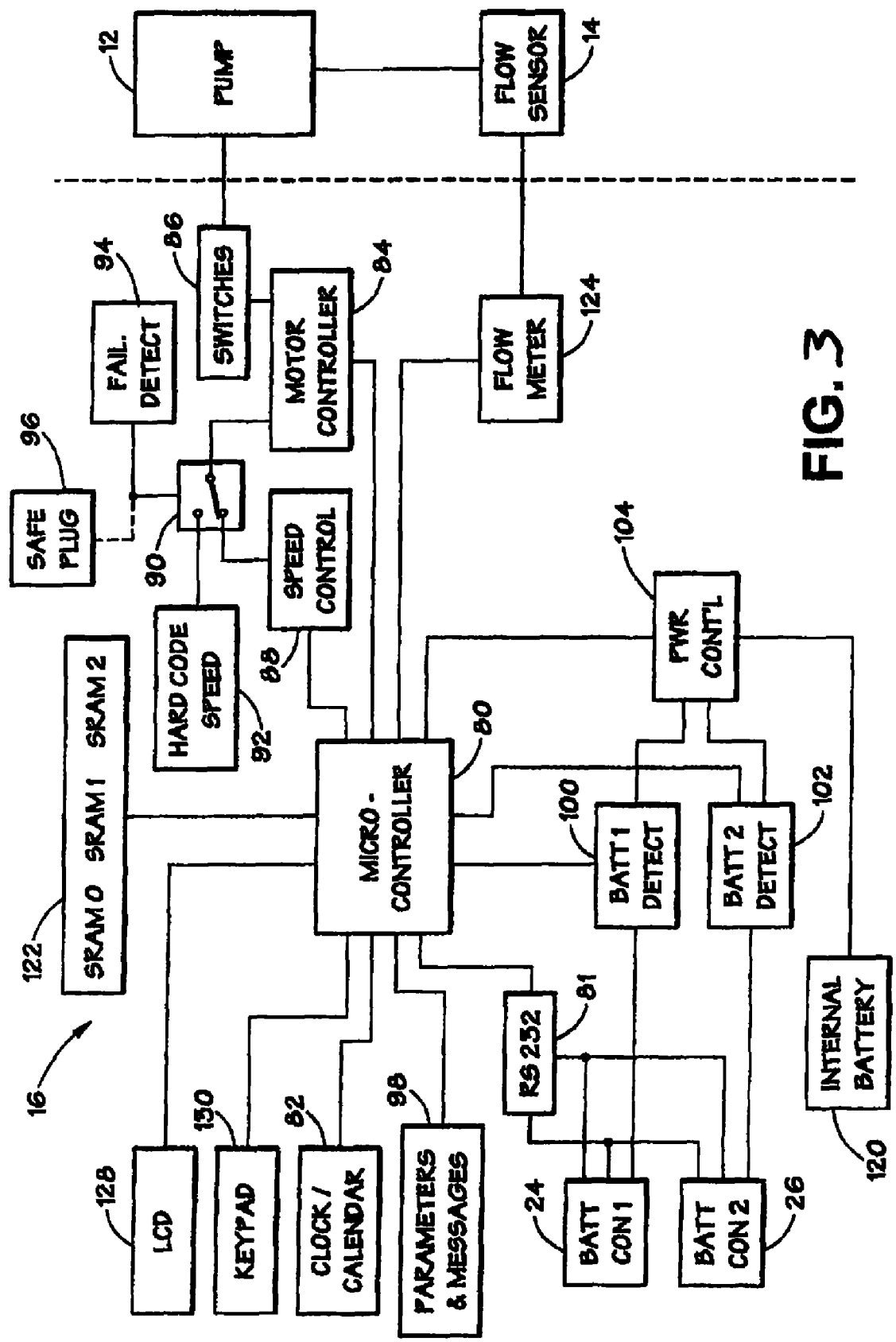
FIG. 3 is a block diagram illustrating additional details of the exemplary pump controller shown in FIG. 2.

The pump controller 16 of an embodiment of the present system is illustrated in greater detail in FIGS. 2 and 3 in block diagram form. The pump controller 16 may be mounted to any suitable support device, such as a user's belt or to a vest worn by the user. The pump controller 16 may include two connectors 24 and 26 for coupling to one or more batteries and/or an internal battery 120, which provide power for the pump controller 16.

The pump controller 16 includes a processor, such as a microcontroller 80, which is coupled to a communications device 81 such as an RS-232 driver/receiver as is known in the art, and a hardware clock and calendar device 82, which contains clock and date information, allowing the pump controller 16 to provide real-time clock and calendar information. The microcontroller 80 preferably communicates with the hardware clock 82, such as by the $I^2C$ protocol or other communication functionality. The microcontroller 80 may also be programmed with a self test routine, which is executed upon application of power to check components of the pump controller 16.

A motor controller 84 is coupled to the microcontroller 80, and the motor controller 84 is coupled to the pump 12. A pump motor speed control circuit 88 is coupled to the microcontroller 80 to receive inputs regarding pump operation parameters. The speed control circuit 88 is coupled to the motor controller 84 through a switching device 90, which couples either the speed control circuit 88 or a hardware-implemented "safe mode" speed setting 92, which is independent of the microcontroller 80.

The microcontroller 80 is adapted to receive analog and digital inputs from a variety of sources, such as through one or more analog to digital converters (A/D) and/or multi-channel A/Ds. In a preferred embodiment, the microcontroller 80 includes a multiple channel A/D, which receives indications of motor parameters from the motor controller 84. Thus, the controller module 16 may monitor parameters such as instantaneous motor current, the alternating current (AC) component of the motor current, the direct current (DC) component of the motor current, and motor speed in revolutions per minute (RPM). In an embodiment of the present invention, the controller module 16 incorporates low pass digital filtering algorithms to calculate the mean values of parameters such as motor current to an accuracy of ±1% of full scale.

As shown in FIG. 3, a series of memory devices 122 are additionally coupled to the microcontroller 80 to save system parameters in the event of an emergency, such as a pump shutdown. In one embodiment of the invention, the memory devices comprise three 128K banks of Static Random Access Memory (SRAM), which store pump parameters such as pump voltage, current, RPM and flow. The first of the three SRAM banks, segment 0, is the "looping bank," which employs a continuous, circular buffer that continuously stores the current performance data. The second SRAM bank, segment 1, contains the pump performance data prior to the first alarm or restart that occurs after initial power-on. The third bank, segment 2, contains pump performance data prior to the most recent restart event. After each restart event (or any alarm if segment 0 is clear) the data in the active looping bank are transferred to segment 0 or segment 1, as appropriate. In one embodiment of the invention, memory segments 0 and 1 each store 55 seconds of pump performance data segments, including pump speed (RPM), voltage, flow rate, instantaneous motor current and time. Further, sample rates for these parameters may be as follows: instantaneous motor current, 2000 samples per second; flow rate, 333 samples per second; pump speed, 10 samples per second; and voltage, 10 samples per second. The sampling resolution for these parameters is eight bits in one embodiment of the invention.

Preferably, the pump's information is monitored, displayed, and stored onto a non-volatile memory device (e.g. hard disk drive). Such pump information typically includes pump speed, pump flow, pump current, and pump power. Other useful and or related information may also be monitored displayed, and/or stored, such as left atrial pressure, aortic pressure, right atrial pressure, pulmonary artery pressure, and differential pressure across each pump.

Since the implanted flow sensor 14 is coupled to the flow meter 124 of the pump controller 16, a true measure of system performance (flow rate) is available for analysis, in addition to pump parameters such as pump speed. Further, flow rate may be displayed on a pump controller display 128, and flow rate data may be saved in the pump controller memory 122 for later analysis.

An Electronically Erasable and Programmable Read-Only Memory (EEPROM) 98 connected to the microcontroller 80, in addition to storing excessive suction detection parameters, stores prompts and messages for display and manipulation via a user interface. The microprocessor communicates with the EEPROM 98, such as the I$^2$C protocol or other communications functionality. As shown in FIG. 3, the pump controller's user interface may comprise the display 128 and an input device 130. In one embodiment, the display 128 comprises a two-row, back-lit 16-character LCD display. The input device 130 may include a keypad, which in an embodiment of the invention, includes two sealed keypad switches to perform the functions of alarm silence and display scroll. The LCD 128 also contains a conventional backlight (not shown), which is automatically lit either by pressing one of the keypad switches 130 or when an alarm is sounded.

The display 128 may be configured to display messages in multiple languages. The message displays may be arranged such that predetermined display character positions are reserved for displaying the parameter or alarm "label," such as "PUMP SPEED." These labels may be stored in one or more languages in the message and parameter EEPROM 98. Other predetermined positions on the display 128 may be reserved for displaying the parameter value reading as received by the controller module.

The pump controller 16 preferably includes an integral flow meter 124. Alternatively, the flow meter 124 may be external to the pump controller 16. In an embodiment of the present invention, the flow meter 124 is preferably coupled between an implanted flow sensor 14 and the microcontroller 80. In a preferred embodiment, at least one flow sensor 14 is implanted down stream of the pump 12. Alternately, a flow sensor 14 may be integrated with the pump 12. In either case, the flow meter 124 is preferably of the type available from Transonic Systems, Inc., such as a Transonic Systems, Inc. model FPT-1072 flow meter board, or the like.

Figure 4:
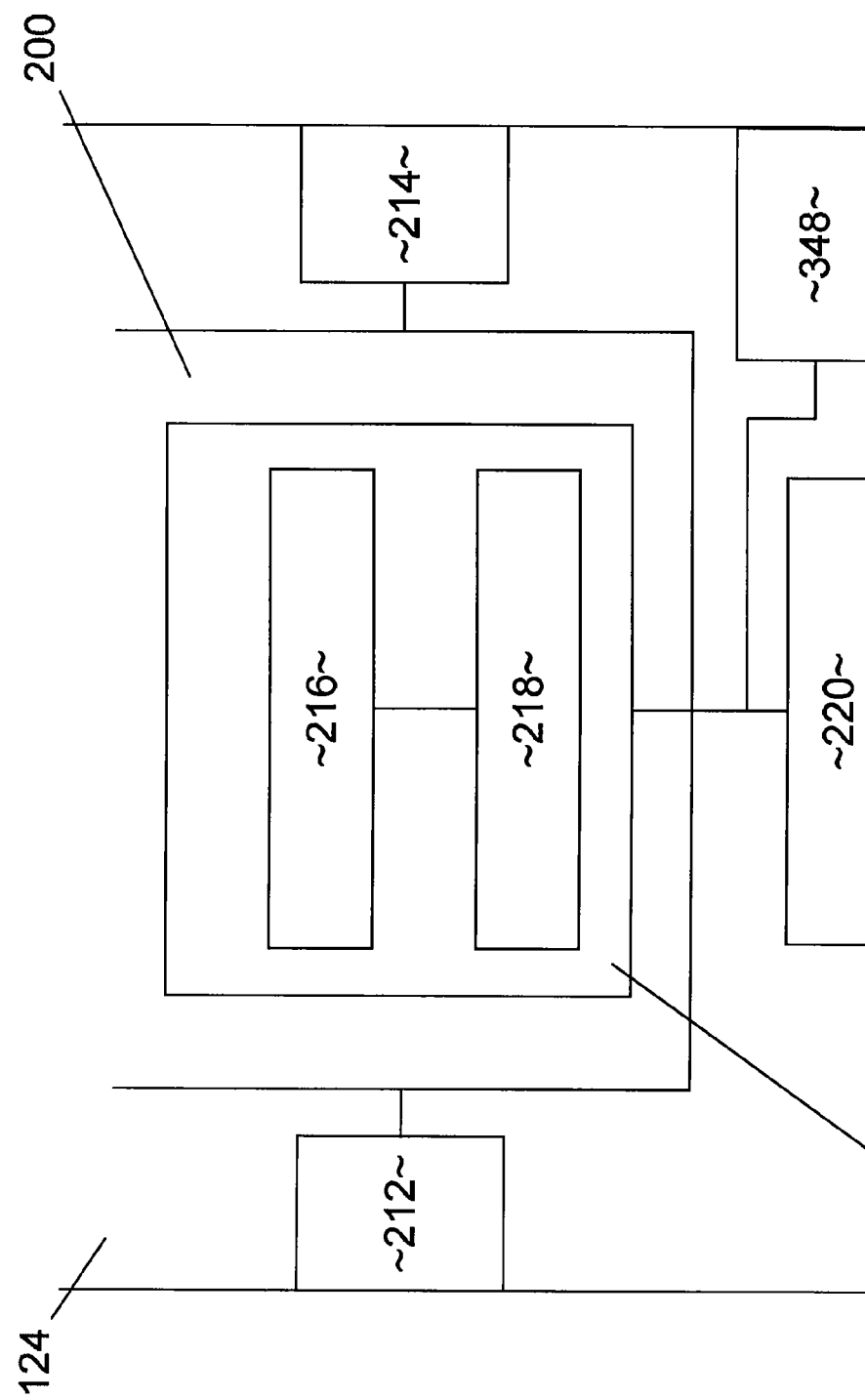
FIG. 4 is a simplified block diagram illustrating a flow meter associated with the exemplary pump controller shown in FIG. 2.

The flow meter 124 receives raw sensor data from the flow sensor 14, herein referred to as the flow signal. The flow meter 124 converts the flow signal to a usable flow rate, for use by the pump controller 16, using a conversion circuit 200, as shown in FIG. 4. The flow meter 124 also includes an input 212, though which to receive the flow signal, and an output 214, through which to communicate the flow rate to the pump controller 16.

The conversion circuit 200 may average the data from one or more flow sensors 14 and outputs the flow rate data to the microcontroller 80 A/D (not shown), allowing the microcontroller 80 to monitor instantaneous flow rate. The amplitude of the flow signal from the flow sensor 14 may also be provided to the microcontroller 80 to monitor system integrity. The accuracy of the conversion circuit 200 is controlled by a digital potentiometer (EEPOT) 210, such as a model X9250 available from Xicor, Inc. Milpitas, Calif., which is essentially used to calibrate the conversion circuit 200.

The calibration is accomplished by way of Gain, Offset, Balance, and Normalization constants. The calibration may also require use of compensation constants, such as temperature, linearization, and age compensation constants. These constants, hereafter referred to as calibration constants, are stored in the EEPOT's 210 onboard non-volatile memory 216. The flow meter 124 uses these constants to improve its accuracy over its full range of flow. The non-volatile memory 216 may also store a serial number, such as an eight digit number, or other identification that can be matched to the stored constants for future reference. The data stored in the nonvolatile memory 216 is externally accessible through the EEPOT's 210 onboard volatile memory 218 and the flow meter's 124 bidirectional communications port 220.

Figure 5:
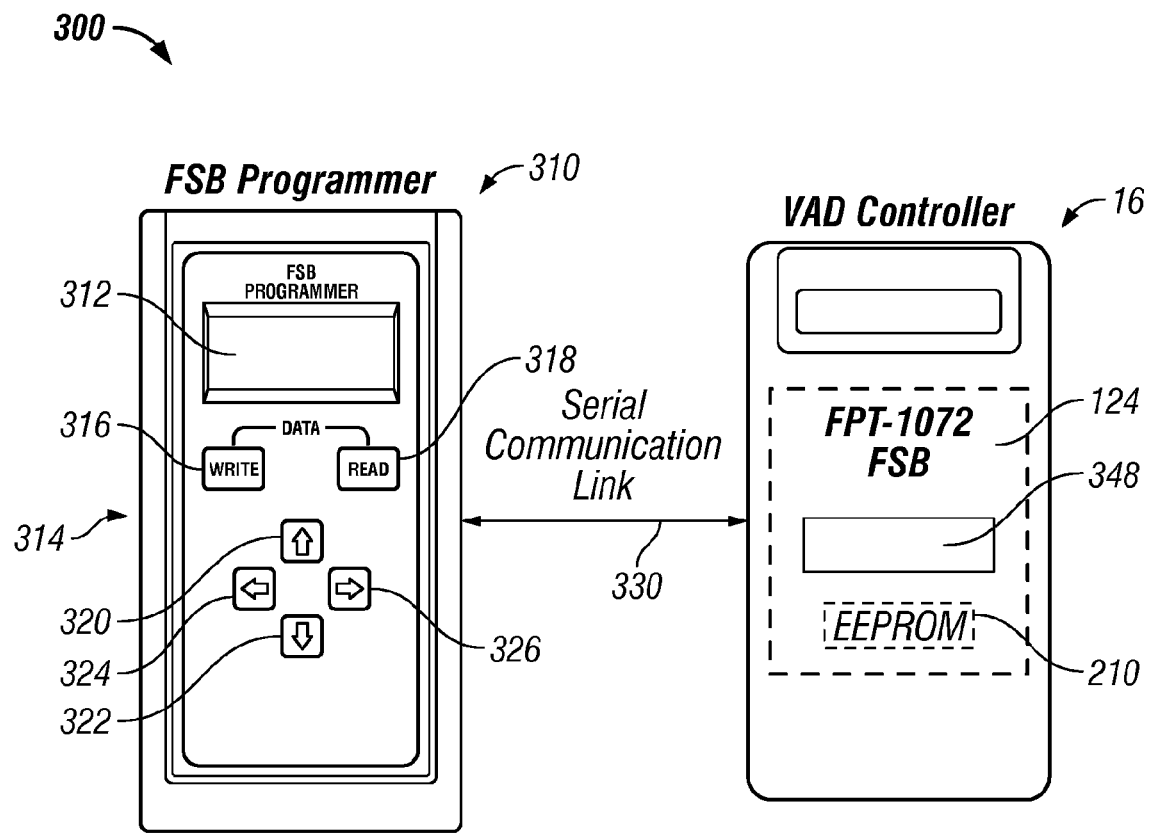
FIG. 5 is a block diagram illustrating a controller programming system in accordance with certain teachings of the present disclosure.
Figure 6:
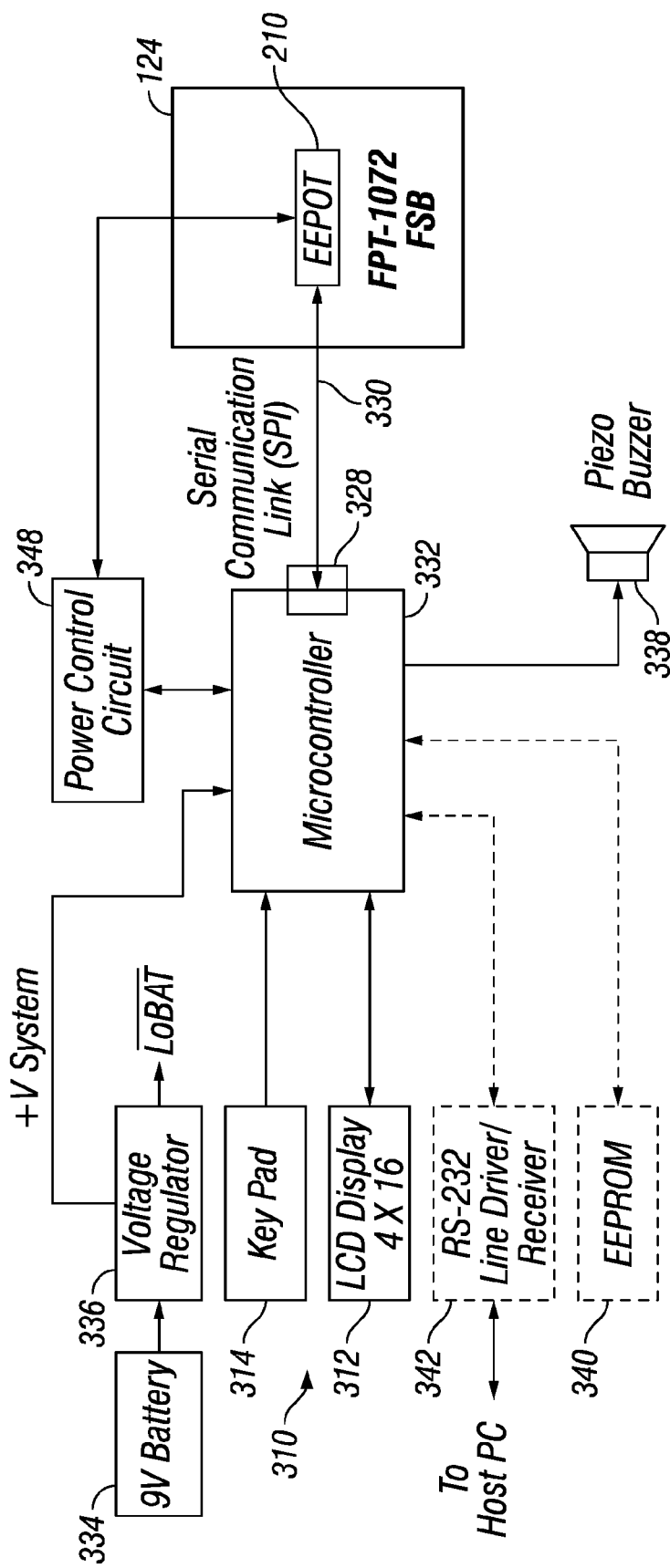
FIG. 6 illustrates additional details of the controller programming system shown in FIG. 5.

The calibration constants and serial number may be written to and read from the EEPOT's 210 memory 216,218 using a programmer 300, such as that shown in FIGS. 5 and 6. The programmer 300 is preferably a small, handheld, battery-powered device that provides a user interface 310 to enable manual entry, retrieval, and verification of the calibration constants and serial number in the flow meter 124. The user interface 310 may comprise a display 312 and an input device 314. In one embodiment, the display 312 comprises a four-row, back-lit 16-character LCD display. The input device 314 may include a keypad, which in an embodiment of the invention, includes six sealed keypad switches to perform the functions of alarm silence and display scroll. The keypad switches 314 preferably include a write key 316 to write data to the flow meter 124, a read key 318 to read the data from the flow meter 124, an increment key 320 to increment a displayed portion of the data, a decrement key 322 to decrement a displayed portion of the data, and both a scroll left key 324 and a scroll right key 326 to scroll through the data on the display 312.

The LCD 312 also contains a conventional backlight (not shown), which is automatically lit either by pressing one of the keypad switches 314. The backlight is preferably turned off automatically after a period has elapsed following the last keystroke. For example, the backlight may turn off after one minute since the last keystroke. Similarly, the programmer 300 itself is preferably turned off automatically after a period has elapsed following the last keystroke. For example, the programmer 300 may turn off after five minutes since the last keystroke. Both periods may be user selectable and vary between thirty seconds and thirty minutes. Alternatively, where the user is unconcerned with battery life, the programmer 300 and backlight may be configured to remain on until specifically turned of my the user.

In addition to reading and writing, the calibration constants and serial number may also be verified in the flow meter 124 using the programmer 300. In order to read, write, and verify the data, the programmer 300 connects to the communications port 220 of the flow meter 124 through a bidirectional communications port 328 and a communications cable 330.

This communications may be serial or parallel in nature. In an embodiment of the invention, the communications ports 220, 328 are serial ports conforming to an industry standard, such as the SPI standard.

The programmer 300 also includes a microcontroller 332 to control the functions of the programmer 330, and an onboard removable and/or rechargeable battery 334 to supply power to the programmer 300 through a voltage regulator 336. The microcontroller 332 is preferably of the type commonly available from Microchip Technology, Inc. of Chandler, Ariz., such as the Microchip PIC16F77. The voltage regulator 336 is preferably capable of indicating when the battery's 334 voltage has fallen below an acceptable threshold. The programmer 300 also includes an audio output 338, such as a piezoelectric buzzer to announce keystrokes and provide alarms, as needed. The programmer 300 may also include a memory 340, such as an EEPROM, to provide operating instructions to the microcontroller 332. The calibration data may also be stored indefinitely in the memory 340.

Figure 7:
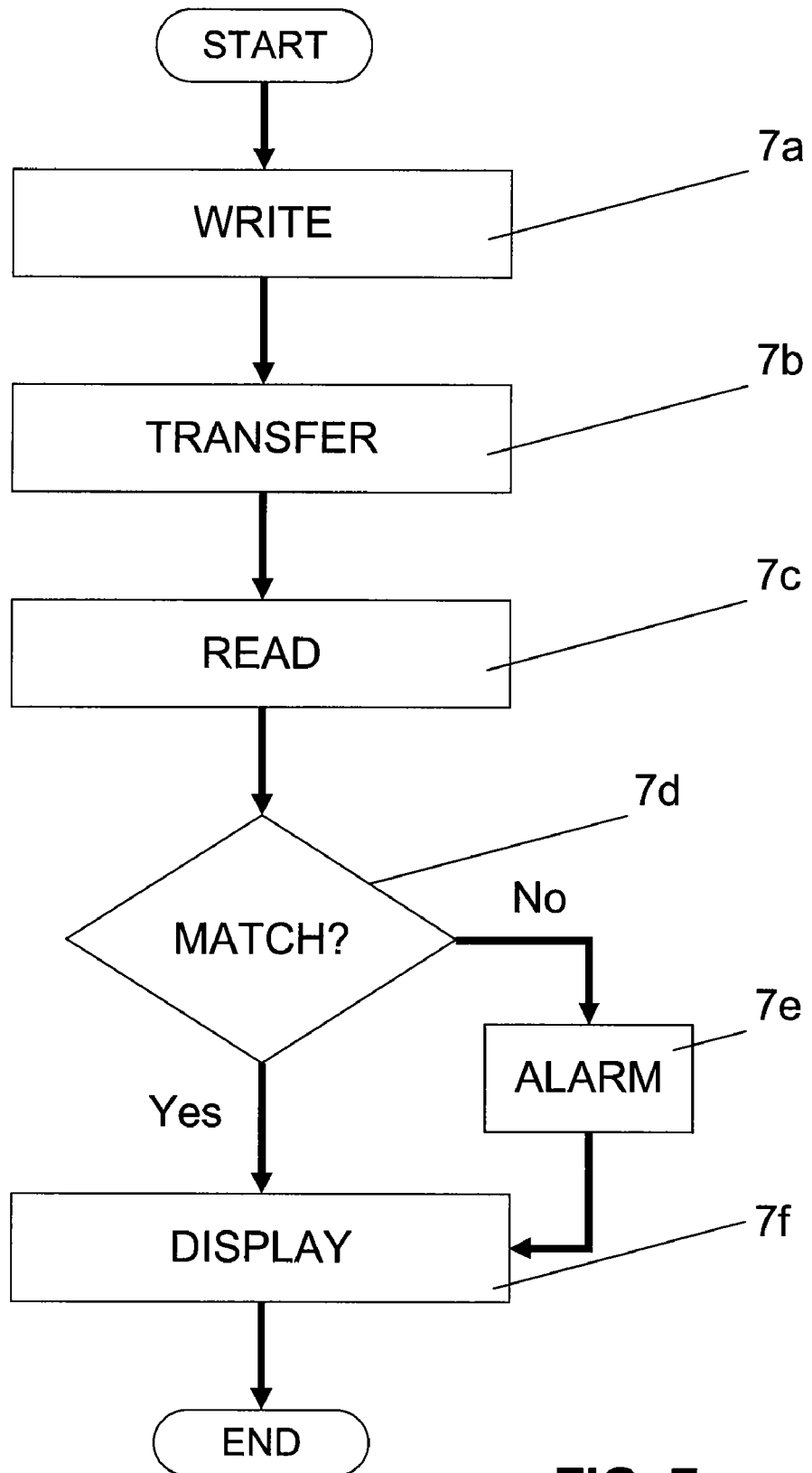
FIG. 7 is a flow chart depicting some of the functionality of the controller programming system.

In use, as shown in FIG. 7, the programmer 300 is commanded to write new data directly to the nonvolatile memory 216, as shown in step 7a, using the write key 316. The new data is transferred from the nonvolatile memory 216 to the volatile memory 218, as shown in step 7b. The programmer 300 is then commanded to read the data from the volatile memory, as shown in step 7c, using the read key 318. Once read by the programmer 300, the data is compared to the intended written data, as shown in step 7d. If the data does not match, an alarm is sounded through the buzzer 338, as shown in step 7e. In either case, the data read by the programmer 300 is then displayed on the display 312, as shown in step 7f. In addition, the written data may be displayed on the display, along with the data read by the programmer 300, thereby providing the operator with a visual verification as well. In this manner, the data in the flow meter 124 may be verified with the data intended to be written to the flow meter 124.

Figure 8:
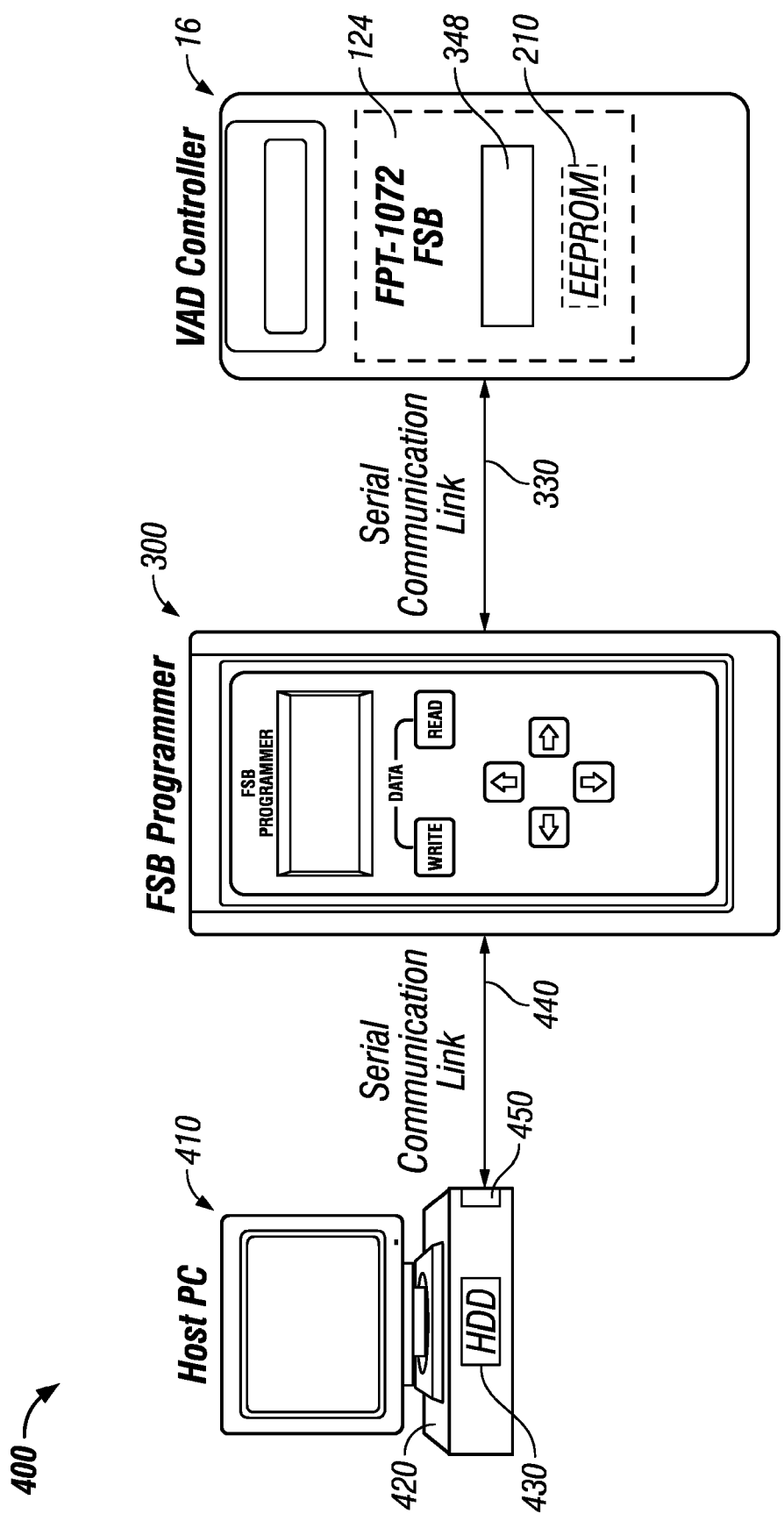
FIG. 8 is a block diagram illustrating certain components of a computer-controlled flow calibration system in accordance with certain teachings of the present disclosure.

The programmer 300 may also be used in conjunction with a host computer 400, such as that shown in FIG. 8. The computer 400 preferably includes a monitor 410 and a central processing unit (CPU) 420. The CPU 420 preferably includes a hard disk drive 430, which may be internal, external, and/or removable. The computer 400 may also include various peripheral devices, such as a keyboard, and/or mouse. The drive 430 of the computer 400 may be used to store data received by the programmer 300 from the flow meter 124. This configuration is particularly useful in storing calibration data long term. For example, the calibration data stored in the drive 430 may be retrieved and used to replace data lost from the flow meter 124, using the programmer 300. Sharing of the data between the programmer 300 and the computer 400 is preferably through a communications cable 440 connected between a bidirectional communications port 342 on the programmer 300 (FIG. 6) and a bidirectional communications port 450 on the computer 400. This communications may be serial or parallel in nature. In an embodiment of the invention, the communications ports 342,450 are serial ports conforming to an industry standard, such as the RS-232 standard or the SPI standard.

More specifically, an operator of the computer 400 may retrieve the calibration data from the drive 430 and send it to the flow meter 124 through the programmer 300. Alternatively, an operator of the programmer 300 may retrieve the calibration data from the drive 430 and send it to the flow meter 124 using the programmer 300. Of course, it may also be accomplished by some combination of the above described steps. For example, the operator of the computer 400 may write the data to the programmer 300. Then, the operator of the programmer 300 may write the data to the flow meter 124. Of course, the operator of the computer 400 and the operator of the programmer 300 may be two different people or the same person.

The invention's capability of retrieving, manipulating, and storing data on the programmer 300 and/or the computer 400 is advantageous. For example, production personnel may use data stored on the computer 400 to prepare the system 10 for field use before the system 10 leaves a production facility. Alternatively, field personnel may retrieve data from the computer 400 and reconfigure the system 10, after deployment, using the programmer 300.

The flow meter 124 preferably includes a power management circuit 348. The power management circuit 348 is preferably incorporated into the Transonic model FPT-1072 flow meter board. Alternatively, the power management circuit 348 may be fully or partially incorporated into, or distributed among, the pump controller 16, the flow meter 124, the EEPOT 210, the programmer 300, or any combination thereof. In any case, the power management circuit 348 detects and supplies power to the EEPOT 210 of the flow meter 124 independently of the pump controller 16 and the flow meter 124. In other words, the power management circuit 348 is capable of providing power to the EEPOT 210 whether or not the EEPOT 210 is powered by the pump controller 16 or the flow meter 124 and do so in a manner that doesn't cause any fault condition between the programmer 300 and the flow meter 124.

Figure 9:
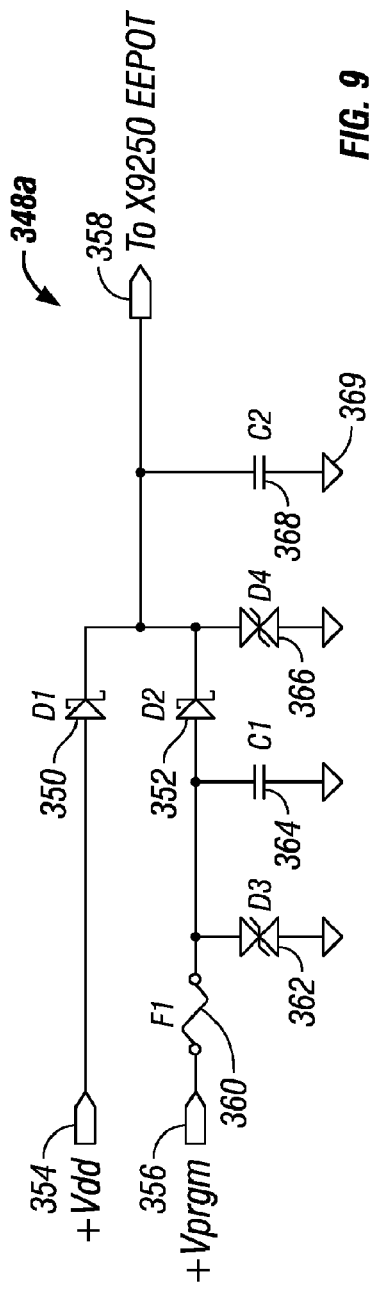
FIG. 9 is a schematic diagram illustrating a first preferred dual power management circuit for use with either the controller programming system of FIG. 5, the flow calibration system of FIG. 8 or both.

FIG. 9 shows one example of a power management circuit for use with the present invention. In this case, the power management circuit 348a includes a first and second diode 350,352 configured to allow power from the programmer 300, the flow meter 124, or both to energize the EEPOT 210. At the same time, power is prevented from flowing from the programmer 300 to the other components of the flow meter 124 or from the other components of the flow meter 124 to the programmer 300. The diodes 350,352 are preferably Schottky diodes. The forward voltage drops of the Schottky diodes 350,352 require that the power from the programmer 300, the flow meter 124, or both be greater than 4.82 volts DC to properly energize the EEPOT 210, which requires 4.5 volts DC.

The power management circuit 348a also includes a flow meter power input (Vdd) 354, a programmer power input (Vprgm) 356, and a power output 358. The Vdd 354 is connected to power supplied from the flow meter 124. The Vprgm 356 is connected to power supplied from the programmer's 300 battery 334 through the communications cable 330. The power output 358 supplies power to the EEPROM 210 whenever there is adequate power available from the Vdd 354, the Vprgm 356, or both. The power management circuit 348a also includes a fuse 360 to address potential power protection issues and protect other components of the programmer 300. The power management circuit 348a also includes third and fourth diodes 362,366 and first and second capacitors 364, 368, communicating to ground 369, to address potential power quality issues, thereby conditioning the power supplied to the EEPOT 210.

Figure 10:
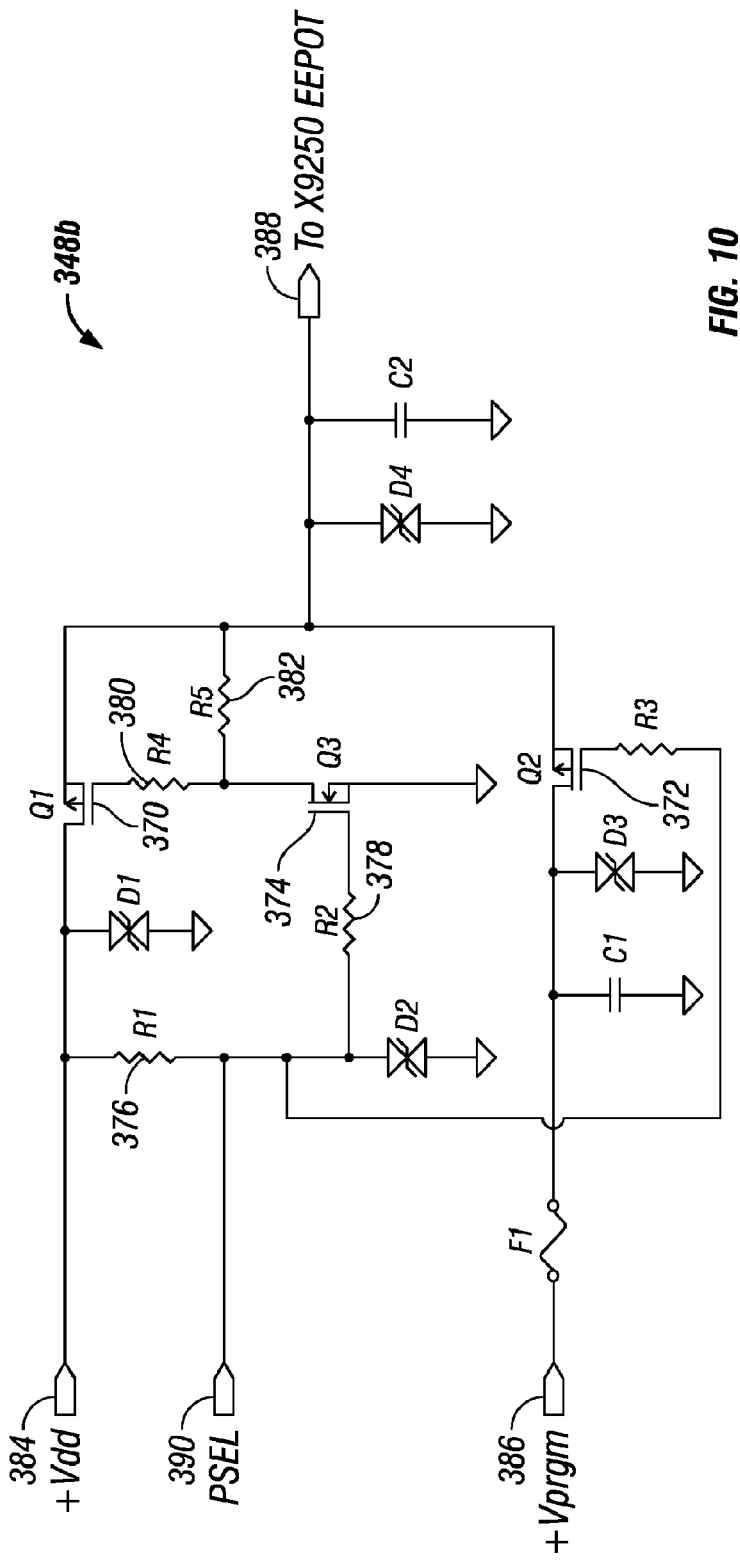
FIG. 10 is a schematic diagram illustrating a second preferred dual power management circuit for use with either the controller programming system of FIG. 5, the flow calibration system of FIG. 8 or both.

FIG. 10 shows another example of a power management circuit for use with the present invention. In this case, the power management circuit 348b includes first, second, and third Metal Oxide Semiconductor Field-Effect Transistors (MOSFET) 370, 372, 274 configured to route power to the EEPOT 210. More specifically, diodes integral to the first and second MOSFETs 370,372 allow power from either the programmer 300 or the flow meter 124 to energize the EEPOT 210, while preventing power from flowing from the programmer 300 to the other components of the flow meter 124 or from the other components of the flow meter 124 to the programmer 300. A resistor network comprising first, second, third, and fourth resistors 376, 378, 380, 382 ensure that the first MOSFET 370 is turned on fully if the power management circuit 348b receives power from the flow meter 124. This configuration takes advantage of power supplied by the flow meter 124, thereby minimizing power drawn from the programmer 300.

The power management circuit 348b also includes a flow meter power input (Vdd) 384, a programmer power input (Vprgm) 386, and a power output 388. The Vdd 384 is connected to power supplied from the flow meter 124. The Vprgm 386 is connected to power supplied from the programmer's 300 battery 384 through the communications cable 330.

The power management circuit 348b also includes a power select input (PSEL) 390 from the microcontroller 332. The PSEL 390 allows the microcontroller 332 to select which source will power the EEPOT 210, while disconnecting the other source, thereby allowing the programmer 300 to control power flow to the EEPOT 210. For example, the PSEL 390 may be pulled low which turns on the second MOSFET 372 and turns off the third MOSFET 374, thereby allowing the third and fourth resistors 380,382 to turn off the first MOSFET 370. The PSEL 390 is communicated to the power management circuit 348b through the communications cable 330.

The power management circuit 348b also includes a fuse 360 to address potential power protection issues and protect other components of the programmer 300. The power management circuit 348b also includes two additional diodes and two capacitors, communicating to ground, to address potential power quality issues, thereby conditioning the power supplied to the EEPOT 210. The power management circuit 348 of FIG. 10 requires that the power from the programmer 300, the flow meter 124, or both be greater than 4.501 volts DC to properly energize the EEPOT 210.

Figure 11:
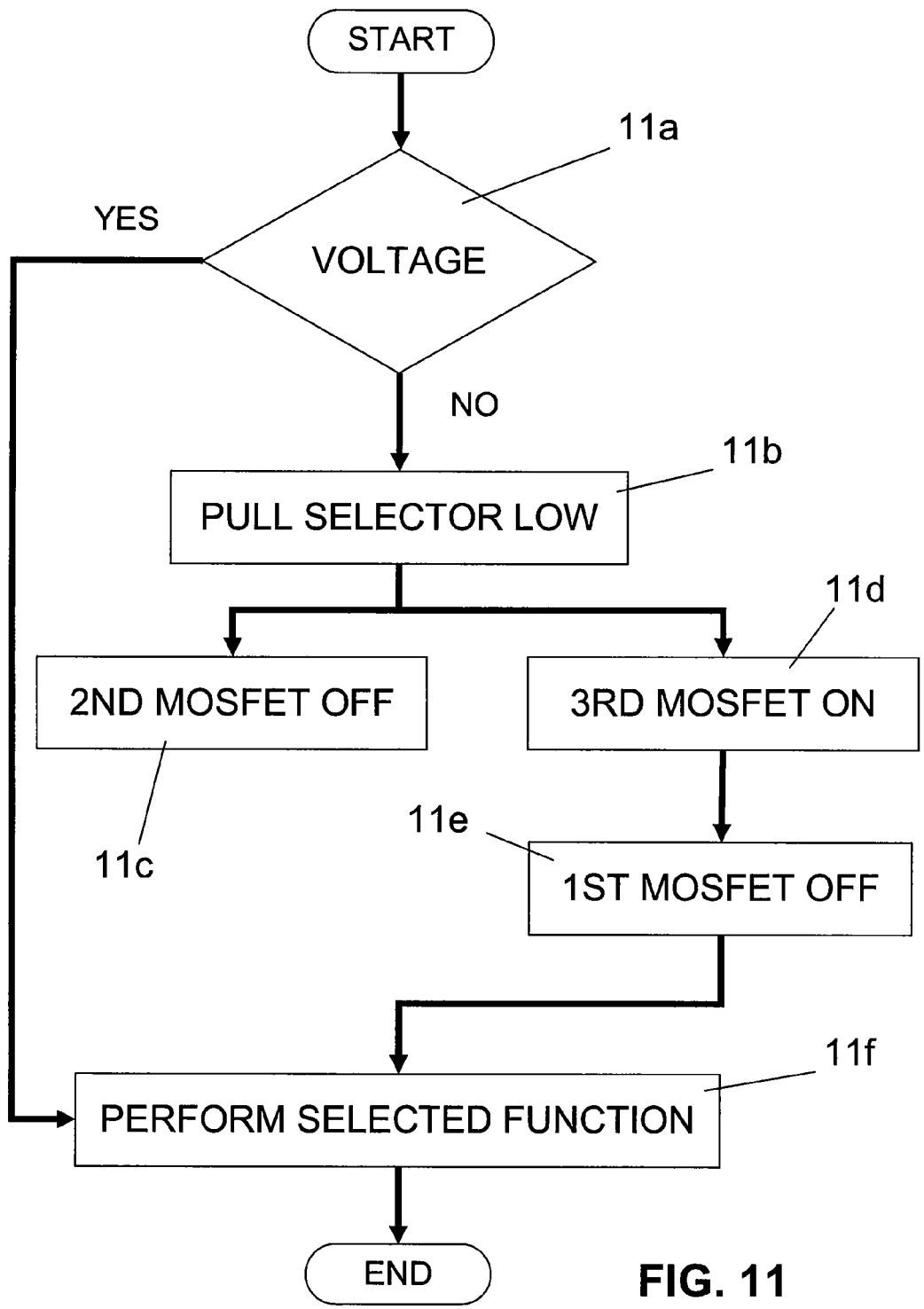
FIG. 11 is a flow chart depicting some of the functionality of the power management circuit of FIG. 10.

In use, as shown in FIG. 11, the programmer 300 first senses whether Vdd 384 is energized, through PSEL 390 and the first resistor 376, as shown step 11a. If Vdd 384 is not energized, the microcontroller 332 pulls PSEL 390 low, as shown in step 11b. As discussed above, this turns on the second MOSFET 372, thereby passing power from Vprgm 386, and shown in step 11c. Pulling PSEL 390 low simultaneously turns off the third MOSFET 374, as shown in step 11d. Turning off the third MOSFET 374 allows the third and fourth resistors 380,382 to turn off the first MOSFET 370, thereby blocking power from Vdd 384, as shown in step 11e. At this point, or if Vdd 384 was energized at step 11a, the programmer 300 performs the function selected by the operator, as shown in step 11f.

Figure 12:
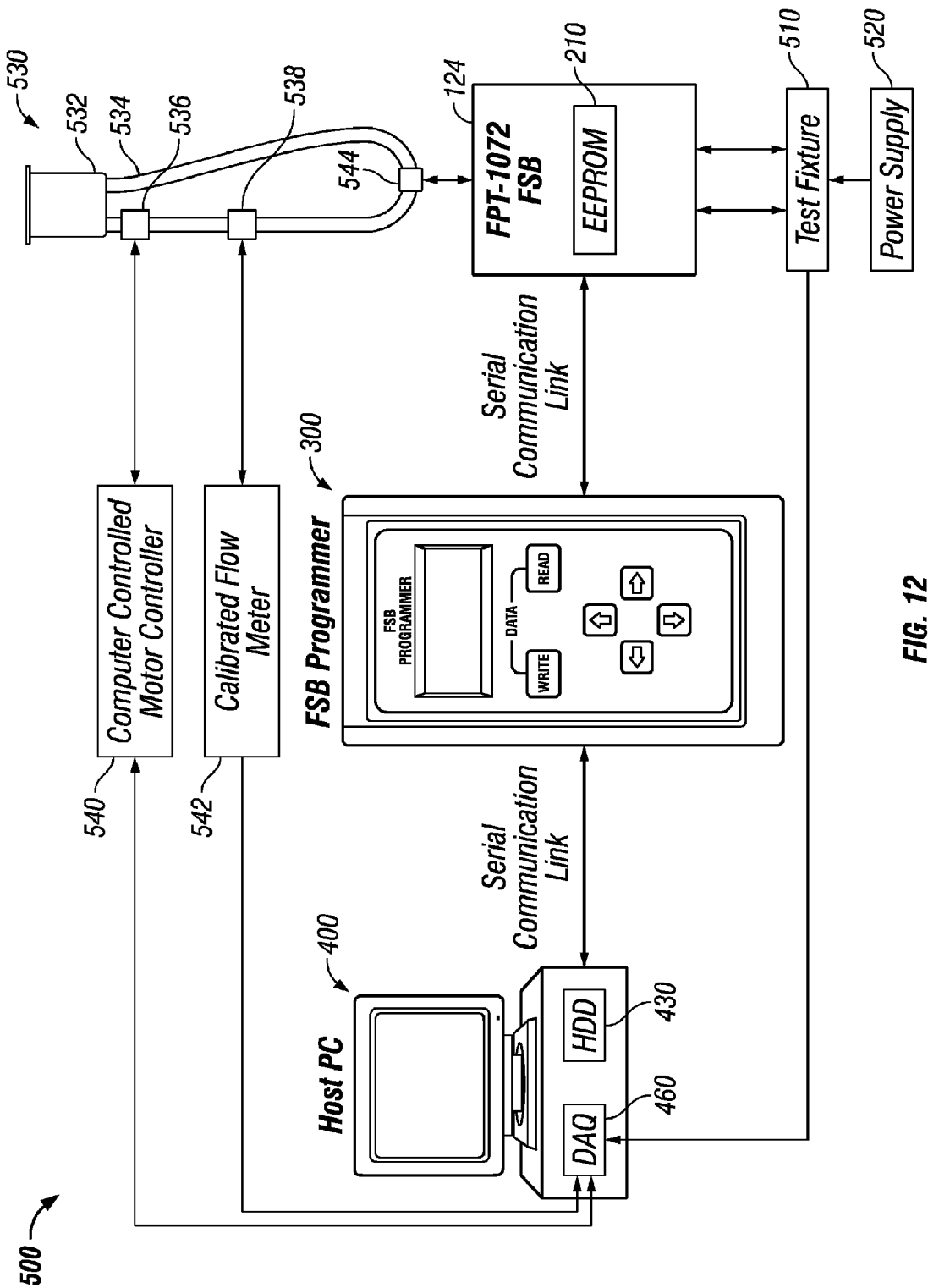
FIG. 12 illustrates additional details of the flow calibration system of FIG. 8.

A computer-controlled flow calibration system 500, as shown in FIG. 12, may be used for initial, periodic, and as needed calibration of the flow meter 124. The calibration system 500 includes the flow meter 124 to be calibrated. The flow meter 124 is preferably supported by a test fixture 510 and powered by a power supply 520, thereby conserving the power available from the programmer's 300 battery. The calibration system 500 also includes the programmer 300 and the computer 400. In this case, however, the computer 400 also preferably includes a control interface 460. the control interface 460 preferably includes both digital-to-analog and analog-to-digital conversion capabilities.

The calibration system 500 also preferably includes a simulated flow system 530, such as a purpose built test system. The test system 530 preferably includes a reservoir 532 for holding a known simulation fluid, such as saline. The test system also preferably includes a closed loop flow path 534 preferably made of resilient tubing, such as TYGON®. In order to pump a known quantity of the fluid through the flow path, the calibration system 500 also preferably includes a pump 536 and a calibrated flow probe 538, such as a commonly available clamp-on calibrated flow probe. Both the pump 536 and the calibrated flow probe 538 are preferably interfaced to the control interface 460 of the computer 400 through a motor controller 540 and a calibrated flow meter 542, respectively. Finally, the calibration system 500 includes a flow probe 544 in communication with the flow meter 124 to be calibrated.

Ideally, as they are to be calibrated together, the flow probe 544 and flow meter 124 are hereafter operationally paired. Such operational pairing ensures that the calibration data acquired by the calibration system 500 remains useful. However, it is possible to extrapolate calibration data between different flow probes and meters, thereby allowing different operational pairings.

Figure 13:
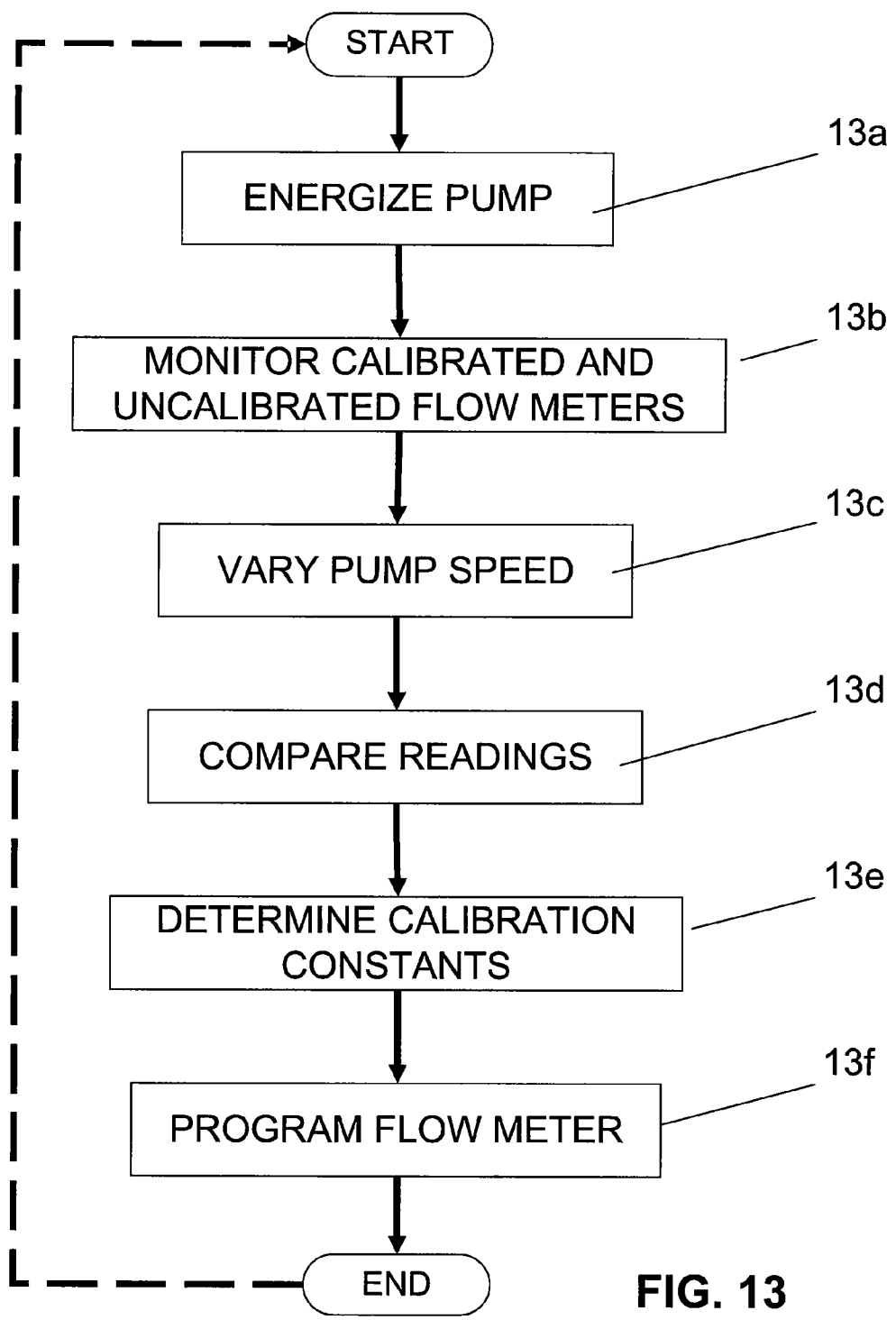
FIG. 13 is a flow chart depicting some of the functionality of the flow calibration system shown in FIG. 12.

In use, as shown in FIG. 13, the computer 400 energizes the pump 536, as shown in step 13a. The computer 400 then begins to monitor both the calibrated flow meter 542 and the flow meter 124 being calibrated, preferably logging both readings, as shown in step 13b. Then, the computer 400 varies the pump's 536 speed throughout the entire range of interest, such as 7500 to 12500 RPM, as shown in step 13c. The computer 400 then compares the readings from the flow meters 124,542, as shown in step 13d, and determines new calibration constants, as shown in step 13e. For example, in an attempt to linearly characterize flow metering, the computer 400 may attempt to draw a "best fit" line, and determine the calibration constants, such as gain and offset, based on that line.

The new calibration data is then written to and verified in the EEPOT 210 using the programmer 300, as shown in step 13f. Once the new data has been verified in the EEPOT 210, the process may be repeated in order to confirm and/or fine tune calibration of the flow meter 124. For example, the process may be repeated once, for two iterations total, to confirm that the flow meter 124 sufficiently matches the calibrated flow meter 542, thereby confirming proper calibration. Alternatively, the process may be repeated indefinitely, until consecutive sets of determined calibration constants match precisely. The second alternative may be required, for example, for initial calibration of newly manufactured flow meters 124 and/or flow probes 544. In either case, the computer 400 preferably logs every aspect of the calibration process, including such details as the serial number(s), date and time of calibration, the logged readings, the determined calibration constants, and calibration conditions, for future reference.

The order of steps, of the above flow charts, can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

Other and further embodiments utilizing one or more aspects of the inventions described above can be devised without departing from the spirit of Applicant's invention. Further, the various methods and embodiments of the invention can be included in combination with each other to produce variations of the disclosed methods and embodiments. Discussion of singular elements can include plural elements and vice-versa.

The inventions have been described in the context of preferred and other embodiments and not every embodiment of the invention has been described. Obvious modifications and alterations to the described embodiments are available to those of ordinary skill in the art. For example, rather that storing calibration data in the drive 430 of the computer 400, the programmer 300 may output the data directly to a printer. The disclosed and undisclosed embodiments are not intended to limit or restrict the scope or applicability of the invention conceived of by the Applicants, but rather, in conformity with the patent laws, Applicants intend to fully protect all such modifications and improvements that come within the scope or range of equivalent of the following claims.

What is claimed is:

1. A blood flow calibration system comprising:
a flow meter having a memory;
a computer operable to determine calibration data for the flow meter; and
a programmer operable to transfer the calibration data from the computer to the memory of the flow meter, wherein the flow meter, computer, and programmer are three separate, connectable devices.

2. The system as set forth in claim 1, wherein the programmer includes a first communications port operable to communicate the calibration data with the computer and a second communications port operable to communicate the calibration data with the flow meter.

3. The system as set forth in claim 1, further including a power management circuit operable to detect whether the memory is powered.

4. The system as set forth in claim 3, wherein the power management circuit is further operable to supply power to the memory when the flow meter is unpowered.

5. The system as set forth in claim 3, wherein the power management circuit is further operable to isolate power from the flow meter when the memory is powered externally from the flow meter.

6. The system as set forth in claim 1, wherein the programmer is operable to transfer the calibration data to the memory without an external power source.

7. The system as set forth in claim 1, wherein the programmer is operable to store the calibration data.

8. The system as set forth in claim 1, wherein the programmer is operable to write the calibration data to the flow meter and verify the calibration data within the flow meter.

9. The system as set forth in claim 1, wherein the programmer is further operable to read the calibration data from the flow meter.

10. The system as set forth in claim 1, wherein the flow meter, computer, and programmer are three separate devices, with the programmer being configured to connect between the flow meter and the computer.

11. The system as set forth in claim 1, wherein the flow meter is part of a pump controller controlling a pump, and wherein the pump controller is a separate device with respect to the computer.

12. A blood flow calibration system comprising:
a flow system operable to simulate blood flow;
a computer operable to determine calibration data for a flow meter using the flow system; and
a programmer operable to receive the calibration data from the computer for use with the flow meter, wherein the flow meter, computer, and programmer are three separate, connectable devices.

13. The system as set forth in claim 12, wherein the programmer includes a first communications port operable to communicate the calibration data with the computer and a second communications port operable to communicate the calibration data with the flow meter.

14. The system as set forth in claim 12, wherein the programmer is operable to transfer the calibration data without an external power source.

15. The system as set forth in claim 12, wherein the programmer is operable to store the calibration data.

16. The system as set forth in claim 12, wherein the programmer is operable to write the calibration data to the flow meter and verify the calibration data within the flow meter.

17. The system as set forth in claim 12, wherein the programmer is further operable to read the calibration data from the flow meter.

18. The system as set forth in claim 12, wherein the flow meter, computer, and programmer are three separate devices, with the programmer being configured to connect between the flow meter and the computer.

19. The system as set forth in claim 12, wherein the flow meter is part of a pump controller controlling a pump, and wherein the pump controller is a separate device with respect to the computer.

20. A blood flow calibration system comprising:
a flow system operable to simulate blood flow; and
a computer operable to determine calibration data for a flow meter using the flow system, wherein the flow meter is part of a pump controller controlling a pump, and wherein the pump controller is a separate device with respect to the computer.

21. The system as set forth in claim 20, further including a programmer operable to transfer the calibration data from the computer to a memory of the flow meter, wherein the flow meter, computer, and programmer are three separate devices, with the programmer being configured to connect between the flow meter and the computer, and wherein the programmer includes a first communications port operable to communicate the calibration data with the computer and a second communications port operable to communicate the calibration data with the flow meter.

* * * * *